United States Patent
Dragnea (10) Patent No.: US 11,202,841 B2
(45) Date of Patent: Dec. 21, 2021

(54) VIRUS-ENABLED TARGETED VECTOR FOR IMAGING

(71) Applicant: The Trustees of Indiana University, Bloomington, IN (US)

(72) Inventor: Bogdan Dragnea, Bloomington, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 68 days.

(21) Appl. No.: 16/545,301

(22) Filed: Aug. 20, 2019

(65) Prior Publication Data

US 2020/0054769 A1 Feb. 20, 2020

Related U.S. Application Data

(60) Provisional application No. 62/719,847, filed on Aug. 20, 2018.

(51) Int. Cl.
| | |
|---|---|
| *A61K 49/00* | (2006.01) |
| *A61P 35/00* | (2006.01) |
| *C12N 7/00* | (2006.01) |
| *A61K 49/18* | (2006.01) |
| *A61B 18/20* | (2006.01) |
| *B82Y 25/00* | (2011.01) |
| *B82Y 5/00* | (2011.01) |

(52) U.S. Cl.
CPC .......... *A61K 49/0097* (2013.01); *A61B 18/20* (2013.01); *A61K 49/0043* (2013.01); *A61K 49/0056* (2013.01); *A61K 49/0065* (2013.01); *A61K 49/1833* (2013.01); *A61P 35/00* (2018.01); *C12N 7/00* (2013.01); *B82Y 5/00* (2013.01); *B82Y 25/00* (2013.01)

(58) Field of Classification Search
None
See application file for complete search history.

(56) References Cited

U.S. PATENT DOCUMENTS

2006/0252130 A1* 11/2006 Boehm .............. A61K 47/6901
435/69.7

OTHER PUBLICATIONS

Aumiller et al. (Chemical Society Reviews. May 2018; 47 (10): 3383-3760).*
Yildiz et al. (Royal Society of Chemistry Advances. 2012; 2: 3670-3677).*
(1) Purcell, E. M. 'Spontaneous Emission Probabilities at Radio Frecuencies', Proc. Am. Phys. Soc. 1946, 681.
(Continued)

*Primary Examiner* — Shanon A. Foley
(74) *Attorney, Agent, or Firm* — Woodard, Emhardt, Henry, Reeves & Wagner, LLP (57) ABSTRACT

A multi-chromophore virus particle is constructed by covalent binding of chromophores and provides super-radiant behavior. A virus-enabled targeted vector is provided for imaging with qualitatively different optical emission properties from state-of-the-art agents. Bright emission is obtained through quantum coherence, which in turn is facilitated by the symmetry of the virus shell. In an exemplary embodiment the targeted vector is used in laser-guided surgery, specifically for the treatment of in brain cancer.

18 Claims, 8 Drawing Sheets
(6 of 8 Drawing Sheet(s) Filed in Color)

(56) References Cited

OTHER PUBLICATIONS

Allen el al.,. 'Amplified Spontaneous Emission and External Signal Amplification in an inverted Medium'. Phys. Rev. A: At., Mol., Opt. Phys. 1973, 8, 2031-2047.
Afton, L. et al., 'Superradiance, Coherence Brightening and Amplified Spontaneous Emission', Phys. Lett. A 1970, 31, 95-96.
Arakawa et al., 'Mechanism of Polyethylene Glycol Interaction with Proteins', Biochemistry 1985, 24, 6756-6762.
Bail, P. 'Physics of Life: The Dawn of Quantum Biology'. Nature 2011, 474, 272-274.
Benedict, M. G., 'Super-Radiance: Multiatomic Coherent Emmission', Institute of Physics Publishers: New York, 1996; p. 326.
Bradac et al., 'Room-Temperature Spontaneous Superradiance from Single Diamond Nanocrystals', Nat. Common. 2017, 8. 1205.
Brilault et al., 'Engineering Recombinant Virus-like Nanopartides from Plants for Cellular Delivery' ACS Nano 2017, 11, 3476-3484.
Cong et al., 'Superradiance in Solids' [invited]. J. Opt. Soc. Am. B 2016, 33, C80.
Dicke, R. H. 'Coherence in Spontaneous Radiation Processes', Phys. Rev. 1954, 93, 99-110.
Dietrich et al., 'An Exciton-Polariton Laser Based on Biologically Produced Fluorescent Protein', Sci. Adv. 2016, 2, No. e1600666.
Gelbart et al., 'Virology: Pressurized Viruses', Science 2009, 323, 1682-1683.
Gopinath et al., 'Replication-indeperdent Long-Distance Trafficking by Viral RNAs in Nicotiana Benthamiana' Plant Cell 2007, 19, 1179-91.
Gross et al., 'Superradiance: An Essay on the Theory of Collective Spontaneous Emission', Phys. Rep. 1982, 93, 301-396.
Khitrova, G. 'H. M. Collective radiance. Nat. Phys.', 2007, 3, 84-85.
Knowles et al., 'Chemical Interactions of Polyethylene Glycols (PEGs) and Glycerol with Protein Functional Groups: Applications to Effects of PEG and Glycerol on Protein Processes', Biochemistry 2015, 54, 3528-3542.
Lang et al., 'Cellular Incorporation of Unnatural Amino Acids and Bioorthogonal Labeling of Proteins'. Chem. Rev. 2014, 114, 4764-4806.
Lehman et al., 'Characterization of Covalently Functionalized Mesoporous Silica Nanoparticles: An NMR Toolbox Approach', J. Phys. Chem. C 2014, 118, 29943-29951.
Lucas et al., 'The Crystallographic Structure of Brome Mosaic Virus', J. Mol. Biol. 2002. 317, 95-108.
Malcuit et al., 'Transition from Superfluorescence to Amplified Spontaneous Emission'. Phys. Rev. Lett. 1987, 59, 1189-1192.
Mattawa Arachchi et al., 'Superradiant Cancer Hyperthermia using a Buckyball Assembly of Quantum Dot Emitters', IEEE J. Sel. Top. Quantum Electron. 2019, 25, 1.
Monshouwer et al., 'Superradiance and Exciton Delocalization in Bacterial Photosynthetic Light-Harvesting Systems', J. Phys. Chem. B 1997, 101, 7241-7248.
Noriega et al., 'Manipulating Excited-State Dynamics of individual Light-Harvesting Chromophores through Restricted Motions in a Hydrated Nanoscale Protein Cavity', J. Phys. Chem. B 2015,119, 6963-73.
Paul, H., 'Photon Antibunching', Rev. Mod. Phys. 1982, 54, 1061-1102.
Pettersen et al., 'UCSF Chimera—A Visualization System for Exploratory Research and Analysis', J. Comput. Chem. 2004, 25, 1605-1612.
Rohou et al., 'CTFFIND4: Fast and Accurate Defocus Estimation from Electron Micrographs'. J. Struct. Biol. 2015, 192, 216-221.
Samuel et al., 'How to Recognize Lasing', Nat. Photonics 2009, 3, 546-549.
Scheibner et al., 'Superradiance of Quantum Dots. Nat. Phys.', 2007, 3, 106-110.
Scheres, S. H., 'RELION: Implementation of a Bayesian Approach to Cryo-EM Structure Determination. J. Struct', Biol. 2012, 180, 519-530.
Scholes et al., (Lessons from Nature about Solar Light Harvesting', Nat. Chem. 2011, 3, 763-774.
Shahbazyan, T. V. Mode Volume, 'Energy Transfer, and Spaser Threshold in PJasmonic Systems with Gain', ACS Photonics 2017, 4, 1003-1008.
Shammah et al., 'Superradiance with Local Phase-Breakino Effects', Phys. Rev. A: At., Mol., Opt. Phys. 2017, 96, 023863.
Skribanowitz et al., 'Observation of Dicks Superradiance in Optically Pumped HF Gas'. Phys. Rev. Lett. 1973, 30, 309-312.
Song et al., 'Fluorescent and Magnetic Anti-counterfeiting Realized by Biocompatible Multi-functional Silicon Nanoshuttle-Based Security Ink Nanoscale', 2018, 10, 1617-1621.
Soto et al., 'Fluorescent Signal Amplification of Carbocyanine Dyes Using Engineered Viral Nano-particles', J. Am. Chem. Soc. 2006, 128, 5184-5189.
Spano et al., 'Superradiance in Molecular Aggregates', J. Chem. Phys. 1989, 91, 683-700.
Spano, F. C., 'The Spectral Signatures of Frenkel Polarons in H-and J-Aogregates', Acc. Chem. Res. 2010, 43, 429-439.
Stepanenko et al., 'Modern Fluorescent Proteins: from Chromophore Formation to Novel Intracellular Applications', BioTechniques 2011, 51, 313-318.
Sun et al., 'Core-Controlled Polymorphism in Virus-Like Particles', Proc. Natl. Acad. Sci. U.S.A. 2007, 104, 1354-1359.
Svidzinsky et al., 'Fermi's Golden Rule Does Not Adequately Describe Dicke's Superradiance', J. Mod. Opt. 2008, 55, 3369-3378.
Tang et al., 'EMAN2: An Extensible Image Processing Suite for Electron Microscopy', J. Struct. Biol. 2007, 157, 38-46.
Tipmeni et al., 'Oncologie Procedures Amenable to Fluorescence-guided Surgery. Ann. Surg.', 2017, 266, 36-47.
Tsien, R. Y., 'Nobel Lecture: Constructing and Exploiting the Fluorescent Protein Paintbox', Integr. Biol. (Camb) 2010, 2, 77-93.
Tsvetkova et al., Radiation Brightening from Vius-like Particles, Indiana University Department of Chemistry, Molecular and Cellular Biochemistry and Physics Departments, Pub. 2019/07/23, [online], [retrieved on Aug. 20, 2019]. Retrieved from the Internet: < URLL ACSNano.org>.
Valeur, 'M. R. N. Molecular Fluorescence: Principles and Applicatians', 2nd ed.; John Wiley & Sons: New York, 2013.
Vrehen et al., 'Superfluorescence: Macroscopic Quantum Fluctuations in the Time Domain', Nature 1980, 285, 70-71.
Wang, Y., 'Guo, L. Nanomaterlal-Enabled Neural Stimulation', Front, Neurosci. 2018, 10, 00069.
Wen et al., 'Design of Virus-Based Nanomaterials for Medicine, Biotechnology, and Energy', Chem. Soc. Rev. 2016, 45, 4074-4126.
Zeng, C., 'Structure and Mechanochemistry of Icosahedral Viruses and Virus Shells Studied by Atomic Force Microscopy', Ph.D. Thesis, Indiana University, 2017.
Zheng et al., 'MotionCor2: Anisotropic Correction of Beam-Induced Motion for improved Cryo-Electron Microscopy', Nat Methods 2017, 14, 331-332.

\* cited by examiner

VIRUS-ENABLED TARGETED VECTOR FOR IMAGING

GOVERNMENT INTEREST STATEMENT

This invention was made with government support under 1740432 awarded by the National Science Foundation. The government has certain rights in the invention.

BACKGROUND

Malignant neoplasm (cancer) currently represents the number one cause of death in the U.S., after heart disease. Early, low-grade tumors are usually treated with surgery alone, followed by close monitoring to make sure there is no recurrence. Success is often predicated upon completeness of tumor removal. In turn, this depends on capabilities of intraoperatively identifying and accessing malignant tissue, ideally down to single cells. Although anatomical and functional imaging techniques such as radiography, computed tomography, magnetic resonance imaging and positron emission tomography have played an important role for accurate preoperative diagnostics, for the most part these techniques cannot be applied intraoperatively.

Fluorescence imaging is becoming a widely used approach for intraoperative guidance in a variety of surgery types, including brain cancer, where minimization of non-malignant tissue removal is crucial. A major impetus in imaging-guided surgery came from the development of targeted fluorescent agents, which by virtue of a physical association of a fluorophore with a targeting moiety (antibody or peptide), can selectively enable detection of specific tissues to a degree nonspecific agents generally do not. For example, brain surgeons currently use a solution of fluorescent markers (referred to as "tumor paint") that bind to receptors on cancer cells, thus helping to identify tissue to be removed (or tissue to be kept). However, small amounts of such fluorescent markers, such as those binding to a single cell, go undetected. Beyond tumor identification, targeting can also be used to intraoperatively identify structures or tissue to be preserved.

Optimization of the pharmacokinetic properties of fluorescent agents has become the focus of numerous research efforts, along with a broadening of the chromophore palette available to fluorescence guided surgery. However, apart from a few notable improvements in photostability and emission wavelength control, the basic phenomena responsible for the optical properties of chromophores in use have remained the same, i.e., spontaneous relaxation after excitation, at the thermodynamic limit.

It is well known that new properties arise when there is a well-defined phase relationship among the microscopic constituents of a material, i.e., when their interactions are coherent. For instance, location of microscopic quantum constituents in a spatially coherent pattern can influence collective temporal coherence via quantum, symmetry-enforced selection rules. Furthermore, while the signal-to-noise ratio for the response of a system of N independent oscillators is proportional to $\sqrt{N}$ at the thermodynamic limit, for a coherent ensemble of oscillators, this ratio is proportional to N, which bears favorably for detection.

Natural systems provide examples in which one encounters quantum coherence at room temperature and in "messy" environments. Specifically, because energy transport at mesoscopic scales can be much more efficient in coherent quantum systems, it is no surprise that some of the molecular processes most central to life on earth appear to rely on quantum coherence. Such is the case for light-harvesting complexes ("LHCs")—macromolecular assemblies in photosynthetic organisms, which exploit the tight spatial organization of self-assembled, proteinaceous, multi-chromophore systems for exciton transport in short times and over distances many times larger than the size of their molecular constituents.

Control of the probability of spontaneous emission via spatial manipulations has a venerable history. In 1954, Dicke noted that, at high densities, N indistinguishable two-level quantum emitters interacting with a common electromagnetic field will tend to organize as a single, massive dipole moment, $\vec{P} = N \cdot \vec{\mu}$, with $\vec{\mu}$ being the transition dipole moment of one chromophore. The spontaneous decay rate (i.e, probability per unit time, γ) is given by the Dirac formula, Equation 1:

$$\gamma = \frac{4}{3} \frac{|P|^2 \omega_0^3}{\hbar c^3} \tag{1}$$

An increase in the magnitude of the transition dipole moment translates into an accelerated decay rate: $\Gamma \sim N/T_1$ through emission of a pulse of duration $\tau_p \alpha T_1/N$, where $T_1$ is the population relaxation time for an independent ensemble of oscillators. Thus Equation 2 gives coherently emitted light intensity scales with N as:

$$I_{coh} \sim N/\tau_p \sim N^2 \tag{2}$$

Figures 1A, 1B:
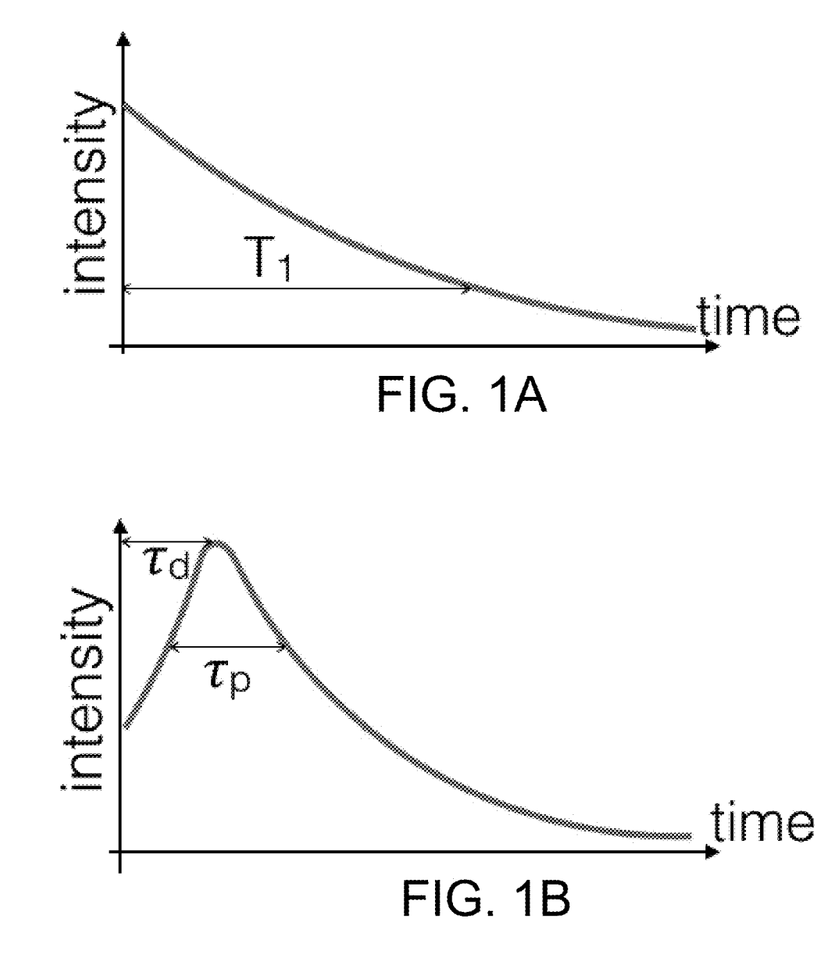
FIGS. 1A-B are a schematic comparison of the general characteristics of spontaneous emission fluorescence and cooperative spontaneous emission.

Referring to FIG. 1, there is shown a schematic comparison of the general characteristics of spontaneous emission fluorescence and cooperative spontaneous emission. Ordinary spontaneous emission "A" is isotropic with an exponentially decaying intensity (time constant $T_1$). Cooperative decay of N quantum radiators has anisotropic emission "B" occurring in a short burst of duration $\tau_p \alpha T_1/N$.

Super-Radiance and Super-Fluorescence

Cooperative emission from an ensemble of multi-level emitters, in the absence of a resonator, can take three forms: super-radiance (SR), super-fluorescence (SF), and amplified spontaneous emission (ASE).

In super-radiance, molecules emit directly from a coherent state formed by the incident laser field. In super-fluorescence, after a rapid intramolecular relaxation step at the end of which the ensemble of emitters is incoherent, a macroscopic dipole forms over a time $\tau_d$ through coupling via vacuum fluctuations, followed by collective emission similar to SR, as predicted by Equation 1. Notwithstanding this element of difference, SR and SF have similar origins, which make them often confused in literature. Since their differences are of no consequence for our purpose, throughout this disclosure the term SR is used to designate any of these phenomena.

In amplified spontaneous emission (ASE), dye molecules absorb light, and start decaying by spontaneous emission. If the emitted light passes through a region containing inverted molecules, it may de-excite these, being amplified in the process. This accelerates the decay, shortening the emitted pulse duration.

Figure 2:
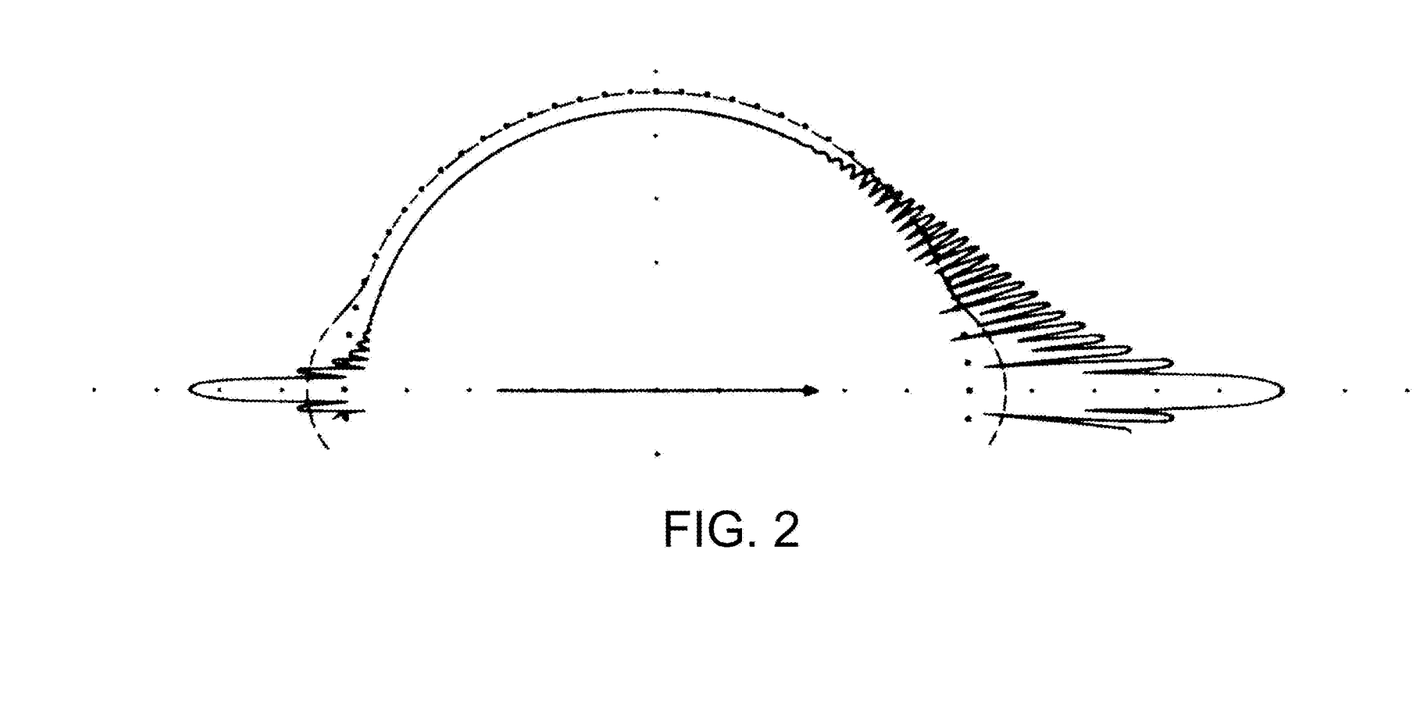
FIG. 2 is a calculated SR emission pattern from two cylindrical regions of Fresnel number=1000 and total volume less than $\lambda 3$, pumped by a laser whose propagation direction is indicated by the arrow. The dashed line is for a small volume (containing just a few chromophores), while the continuous line is for a volume 100 times larger.

Because the gain is strongest at the wavelength where the cross-section for stimulated emission is highest, band narrowing is observed. Within a pumped region, ASE will occur in the direction of the highest gain, which is in general the direction in which the pumped region is most extended. In single particle experiments with isotropic samples, ASE emission probability will be isotropic (each particle will emit in a random direction). However, in SR, the emitted radiation pattern strongly depends on the propagation direction and the polarization of the pump beam, as shown in FIG. 2. Therefore, the difference in emission anisotropy could be harnessed to discriminate between ASE and SR.

Referring to FIG. 2, there is shown a calculated SR emission pattern from two cylindrical regions of Fresnel number=1000 and total volume less than $\lambda^3$, pumped by a laser whose propagation direction is indicated by the arrow. The dashed line is for a small volume (containing just a few chromophores), while the continuous line is for a volume 100 times larger. The dotted line represents spontaneous emission, which is isotropic. One other interesting difference between SR and ASE is that, in ASE no more than half of the initial energy is consumed by the radiation pulse, while in SR all energy could be converted into radiation.

To increase the likelihood of SR over ASE, one has to decrease the time to collective dipole formation ($\tau_d$) or slow down the rate of dephasing processes. The first could be accomplished by reinforcing collective response through addition of a plasmonic exchange coupling between radiators. The second could be accomplished through a reduction of inhomogeneous broadening (see below) by suppressing dynamics along some of the molecular degrees of freedom, as when rigidly binding chromophores onto a template at identical local environments.

A brief look at the factors determining the magnitudes of $\tau_d$ and $\tau_p$ brings forth further insight into potential control parameters. Thus, for an ensemble of two-state atoms, the collective decay time is given by Equation 3:

$$\tau_R = \frac{8\pi S}{3N\lambda_0^2} T_1 \quad (3)$$

In terms of structural parameters, a small S and a large N favor short $\tau_p$. These conditions are naturally satisfied in Virus Like Particles (VLPs).

In addition, to avoid decoherence the cooperative frequency $\Omega_c$ must exceed the decoherence rate as shown in Equation 4:

$$\Omega_c = \sqrt{\frac{2G\omega_0\mu^2\Delta n}{\epsilon\hbar}} > \frac{1}{T_1}, \frac{1}{T_2} \quad (4)$$

where G is the overlap factor of the electromagnetic radiation mode with the active medium emission, $\Delta n$ is the population inversion density, and $\epsilon$, is the dielectric constant of the medium. According to Equation 3, decoherence can be avoided by increasing the population inversion density, which will be achieved in this work via ultrafast laser pumping.

Dipole-dipole coupling, combined with intramolecular non-radiative relaxation, may cause decoherence and suppression of SR. This is why fluorescence emission is quenched in concentrated solutions of pigments. However, while emission from a 0.1 M chlorophyll solution is completely quenched, chlorophyll bound in light harvesting complexes (LHCs) of certain photosynthetic bacteria reaches concentrations of 0.25-0.5 M, yet the LHCs are strongly fluorescent, i.e. concentration quenching is effectively suppressed. The reason for this difference is believed to be that organization of chlorophyll molecules in photosynthetic LHCs is not random. The conceptual link that could be drawn between super-radiant VLPs and LHCs is substantiated by one additional observation. Cooperative spontaneous emission phenomena have been reported for the LH-2 photosynthetic antenna complexes. Results suggest that geometric and scale similarities between VLPs and LHCs lead to similar suppression of fluorescence quenching in VLPs.

Collective Relaxation in the Vicinity of a Nanoparticle Surface

While the original Dicke collective relaxation via free-space emission was observed in a large variety of systems ranging from atomic gases to solid films of conjugated polymers, and to clusters of quantum dots, its extension to collective relaxation in the vicinity of a metal nanoparticle (NP) surface has only relatively recently begun to attract attention.

The basic photophysics of a single quantum emitter in the vicinity of a metal surface and of a metal nanostructure is now well understood. Notably, even in this case, a qualitative leap in understanding occurred only after accurate control over the surface-chromophore distance was established.

The dependence of ensemble fluorescence vs. distance to the metal surface was studied experimentally by Dulkeith et al. on 12 nm diameter Au NPs, with N≈50 chromophores attached by flexible ligands at the end of ssDNA oligonucleotides. Data reported by Dulkeith et al. was consistent with uncorrelated emission from individual chromophores. However, such experiments were characterized by random fluctuations in chromophore density, orientation, and location on the surface. Moreover, the number of chromophores per particle was ~4 times lower than the maximum disclosed herein.

Emission from dye-doped shells encasing a metal NP has been explored experimentally, with the dielectric dye-doped shell playing the role of gain medium compensating the losses in the localized surface plasmon resonance. This loss compensation scheme was proposed to be strong enough to lead to plasmon-assisted nanolasing, and recognized as a possible technological breakthrough for biomedical applications. Chromophore location was random. High dye densities would increase the chances for some dipole pairs to be at sufficiently close distances to prevent formation of SR states. Moreover, inhomogeneous broadening due to variability in chromophore environment could suppress SR, while other emission brightening phenomena (e.g., ASE) would remain unaffected by randomness, their presence obscuring potential observation of SR effects.

In 2009, Pustovit and Shahbazyan suggested that in presence of a metal NP, coupling to the surface plasmon resonance, and plasmon exchange between dipoles, may involve both bright and dark plasmon modes, and thus cooperativity could be more efficiently realized in a VLP than through photonic coupling, which is the only mechanism for cooperativity in the absence of a NP. Furthermore, the plasmonic Dicke effect was postulated to be insensitive to nonradiative transitions. Temnov and Woggon predicted the collective spontaneous emission from an inhomogeneously broadened ensemble of two level systems coupled to a low-Q resonator to follow a two-step decay in which the first step is superradiant and the second is subradiant.

From these examples, the conditions under which plasmon-mediated coherent relaxation may occur have begun to be understood. The VLP approach promises to deliver sufficient structural and dynamic control for the realization and study of plasmonic Dicke effects.

The ability of virus proteins to self-assemble into precise structures that offer a three-dimensional scaffold for functionalization has led to applications of VLPs as optical contrast agents and related biophotonics applications. The steady-state optical properties of a variety of dye-conjugated VLPs have been studied. Quenching was observed at high dye densities, under steady-state excitation.

Virus mimics of light-harvesting complexes constructed from tubular virus scaffolds and organic dyes were studied in relation with artificial photosynthesis applications. Chromophore coupling was genetically engineered and shown to affect the interplay between coherent and incoherent exciton transport. Restricted motion of chromophores bound to a virus template was shown to strongly influence excited state dynamics.

Previous observations suggest that quantum coherence via structural control is likely possible at room temperature when using virus-template approaches. However, neither the cooperative emission in virus-supported chromophore arrays, nor its potential biophotonic applications, has been pursued. In addition, photonic and plasmonic collective relaxation in VLPs are governed by different interactions and selection rules than excitons.

SUMMARY

In certain aspects, the present disclosure provides unique virus like particles. In accordance with some forms of the invention, such virus like particles include a capsid comprising coat protein, and an array of chromophores attached to the capsid. In certain embodiments the capsid is derived from Brome Mosaic Virus. In certain embodiments the capsid is derived from Blue Tongue Virus. In accordance with some forms the capsid may express chlorotoxin. In some forms the capsid further comprises an internal cavity including a metal nano-particle. In some embodiments the array of chromophores is derived from fluorescein. In certain embodiments the coat protein is modified to carry a fluorescein protein. In accordance with certain inventive aspects the capsid may form a nanorod. In certain embodiments the capsid is icosahedral. In accordance with certain preferred embodiments the capsid is derived from a non-envelope virus. In some forms the capsid has an average diameter of less than 150 nm.

In another embodiment the disclosure provides a method of forming a virus-like particle, comprising obtaining a obtaining a virus capsid having surface-reactive groups, and chemically conjugating an array of chromophores with the surface-reactive groups. In certain embodiments the step of chemically conjugating comprises treating the virus capsid with maleimide. In certain inventive variants the array of chromophores is derived from fluorescein. In accordance with some methods the capsid is derived from Brome Mosaic Virus. In certain embodiments the Brome Mosaic Virus comprises a V168C mutant.

In another embodiment the present disclosure provides a method of treating cancer, comprising: exposing patient tissue to a solution containing virus-like particles under conditions effective to allow binding of at least a portion of the virus-like particles to patient tissue, wherein the virus like particles include one or cancer detecting moieties, washing the exposed area to remove unbound particles; scanning patient tissue with a light source sufficient to activate the virus-like particles, and detecting the emission of pulses of near-infrared light indicating bound virus-like particles. In some forms the emission of pulses of near-infrared light by the virus-like particles is sufficient to destroy the bound cancer cell. In certain embodiments the detecting is performed with a pulsated laser scalpel configured to destroy underlying cells upon detection of pulses of near-infrared light by the virus-like particles.

BRIEF DESCRIPTION OF THE DRAWINGS

The patent or application file contains at least one drawing executed in color. Copies of this patent or patent application publication with color drawings will be provided by the Office upon request and payment of the necessary fee.

DESCRIPTION

Where the definition of a term departs from the commonly used meaning of the term, applicant intends to utilize the definitions provided below, unless specifically indicated otherwise.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise.

For purposes of the present invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "comprising", the term "having", the term "including," and variations of these words are intended to be open-ended and mean that there may be additional elements other than the listed elements.

In certain embodiments the present disclosure provides materials and methods useful for in-vivo imaging. In some forms the present disclosure provides virus particles comprising a capsid which has been modified to display a multi-chromophore array. These virus-like particles (VLPs) can be advantageously utilized to image minute quantities of a target moiety as discussed herein. For example, in some forms the virus-like particles of the present disclosure may be used in a method for detecting cancer cells in a patient.

The present disclosure includes materials and methods utilizing virus-like particles. In some forms the virus-like particles comprise a capsid comprising one or more coat proteins. In certain embodiments the capsid comprises a shell formed from a regular arrangement of a coat protein. In some forms the capsid comprises or is derived from icosahedral viruses. In certain embodiments the virus-like particles comprise or are derived from nonenveloped viruses. Thus, in certain embodiments the virus-like particles of the present disclosure may comprise Brome Mosaic Virus (BMV) capsid or a derivative thereof. In some embodiments, the virus-like particles of the present disclosure may comprise Blue Tongue Virus (BTV) capsid or a derivative thereof.

In certain embodiments the virus like particles of the present disclosure may comprise nanorods formed from virus coat protein. For example in some forms the present disclosure provides nanorod virus-like particles which have been modified to display a multi-chromophore array.

In accordance with certain forms the disclosure provides a composition comprising VLPs having an average diameter of less than 150 nm. In preferred embodiments the disclosure provides a composition comprising VLPs having an average diameter of less than 100 nm. In some forms, the disclosure provides a composition comprising VLPs having an average diameter of less than 80 nm. In accordance with certain inventive variants the disclosure provides a composition comprising VLPs having an average diameter in the range of 10 nm to 100 nm, preferably 15 nm to 90 nm, more preferably 20 nm to 80 nm.

In certain embodiments the present disclosure provides a composition comprising VLPs having an average internal cavity diameter of less than 100 nm, preferably less than 75 nm, even more preferably less than 50 nm. In accordance with certain inventive variants the disclosure provides a composition comprising VLPs having an average internal cavity diameter in the range of 5 nm to 75 nm, preferably 10 nm to 60 nm, even more preferably 40 nm to 50 nm.

In accordance with certain forms the virus-like particles of the present disclosure may further include one or more moieties for detection of one or more targets. For example, the virus-like particles may include a targeting moiety configured to detect surface antigens of cancer cells. In certain embodiments the virus-like particles of the present disclosure include chlorotoxin configured to bind cancer cells, for example glioblastoma cells.

Thus, in certain embodiments the present disclosure provides methods of detecting and treating certain conditions, for example cancers. In some forms patient tissue suspected of including target cells (e.g. cancer cells) is exposed to a composition of virus-like particles as described herein, having targeting moieties for a specified target cell type. In some forms the composition is allowed to incubate for a time and under conditions effective to allow at least a portion of the virus-like particles to bind to the target tissue. In certain embodiments the tissue is washed to remove all or substantially all of the unbound virus-like particles. In certain embodiments the treated tissue is then exposed to a light source (e.g. via scanning) sufficient to activate the virus-like particles. In some modes of practicing the disclosed methods the emission of pulses of near-infrared light is detected from indicating the presence of target cells. In some modes, the emission of pulses of near-infrared light by the virus-like particles is sufficient to destroy the bound cell. As will be discussed further herein the emission of pulses of near-infrared light by the activated virus-like particle can be detected by a specialized instrument used to further destroy or remove the bound cells.

Multi-Chromophore Particles

The photophysical properties of multi-chromophore particles are significantly different from those of individual chromophores due to features such as: a volume much smaller than the wavelength of light, high chromophore densities, and near perfect spatial coherence. Moreover, a metal NP modifies in a substantial way the spectroscopic properties of molecules located nearby.

Synthetic approaches include: bioconjugation, Nano Particle-templated assembly, and a synthetic biology approach which will be discussed herein. The latter approach warrants nearly monodisperse samples in terms of architecture, number of chromophores, and targeting moieties.

Applicants have surprisingly discovered that the VLPs produced by the presently disclosed techniques benefit from organizational principles present in viruses to obtain collective behavior from hundreds of chromophores working together, and develop a novel type of imaging vector. In certain embodiments, the structural fidelity of self-assembled VLPs is harnessed to create a targeted, superradiant biophotonic imaging vector.

Figures 3A, 3B, 3C:
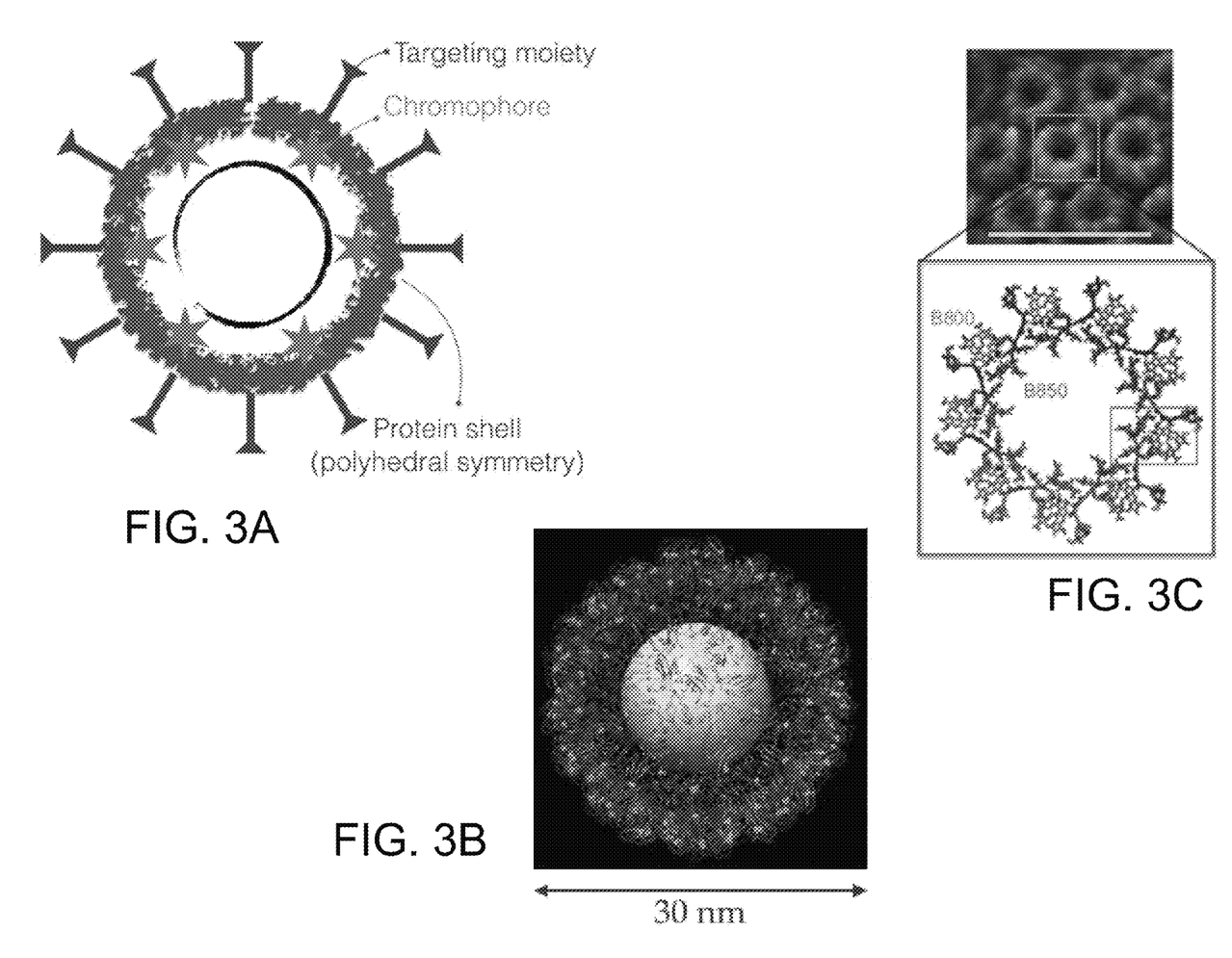
FIGS. 3A-C illustrate exemplary embodiments of virus-like particles according to the present disclosure.

Referring to FIG. 3, shown are exemplary embodiments of VLPs as provided by the present disclosure. Image "A" shows a targeted VLP with a coupled-chromophore array and targeting peptides expressed at the surface of a protein capsid. The black ring represents encapsulated nucleic acid. Image "B" is a molecular model of a VLP based on the BMV mutant V168C with 180 chromophores (green) covalently bound to surface cysteines and an 11 nm diameter metal nanoparticle inside, instead of nucleic acid. Image "C" depicts a structural model of one of the light harvesting complexes (LH2 from *Rps. acidophila*) with chromophores organized in two concentric rings and an atomic force microscopy (AFM) image of a group of LH2s.

In some forms the present disclosure provides for the encapsulation of noble metal particles inside symmetric VLPs. This technique provides a pathway towards enhancements of optical characteristics via near-field coupling of collective excitation energy into surface-plasmon excitations. Applications that go beyond the biomedical realm benefit from, e.g., chemical applications of localized electromagnetic resonances, in particular those related to hot-electron generation for photocatalysis, and light-management at nanoscale.

Full characterization of collective behavior is shown by absorption, excited state dynamics, and emission processes. Theoretical modeling investigates the role of symmetry and guide data interpretation. Nano Particle-templated assembly allows studies of surface plasmon-chromophore array coupling, and substantial control over shell size and shape. In accordance with certain embodiments, a plant-based system for transient expression of engineered BTV structural proteins is used to obtain high yields of VLPs, decorated with red fluorescent proteins (RFP) and chlorotoxin, for targeting. The approach offers the benefits of suppressing particle-toparticle variability, combined with full in planta assembly and loading of the two functional moieties required for targeted imaging.

The fidelity of biological assembly, as disclosed herein, provides for symmetry and identity of the chemical environments of chromophores, and therefore, for reduced inhomogeneous broadening. Therefore, for certain applications requiring deep subwavelength light sources, methods based on genetic manipulation and directed assembly lead to modalities of lowering nanolasing thresholds for optical pumping.

Preparation of VLPs

In certain embodiments, the coat protein of a virus is mutated to express chlorotoxin. Chlorotoxin is a homing peptide used for glioblastoma detection. In accordance with some forms, assembly occurs by spontaneous organization of protein and cargo. In certain embodiments assembly occurs by expression and self-assembly of modified coat proteins in plants. The VLPs of the present disclosure may also include a cargo unit within the VLP. In some forms the cargo comprises non-genomic nucleic acid. In certain embodiments the cargo comprises a nanoparticle. In some forms, the assembled virus-like particle is either (1) decorated with a chromophore derived from fluorescein (e.g., maleimide-functionalized Oregon Green), or (2) the coat protein is modified to carry a fluorescent protein.

Assembly of the VLPs may be accomplished in at least two ways. In some forms, BMV can easily be assembled in vitro and chromophores can be chemically conjugated to it via surface-reactive groups (native or engineered). In some forms, BMV-like shells of different magic numbers of proteins can be assembled by Nano Particle-directed assembly. In accordance with certain embodiments, BTV, whose structural proteins assembly into VLPs, when expressed in plants, and can be genetically engineered to express fluorescent proteins and targeting peptides.

BMV

Figure 4A:
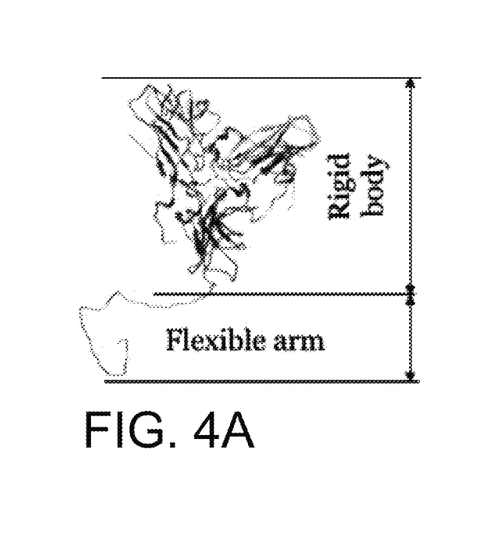
FIGS. 4A-C illustrate exemplary embodiments of virus-like particles according to the present disclosure.
Figure 4B:
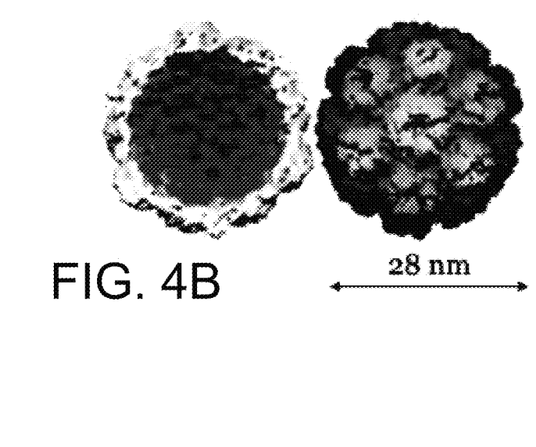
Figure 4C:
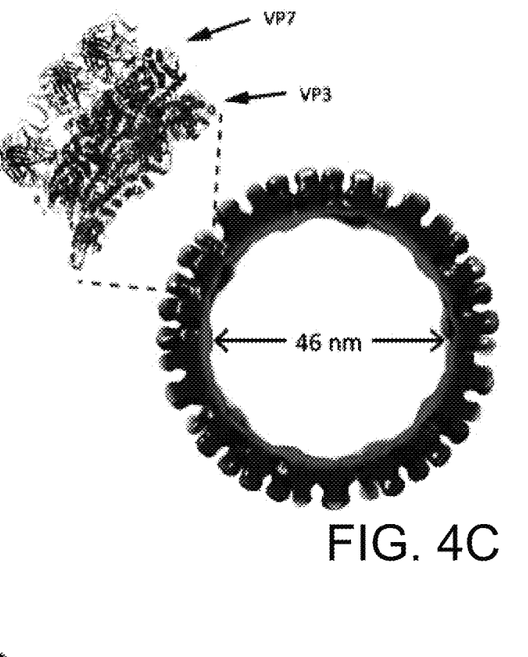

BMV provides a suitable starting system because its structure and chemical properties are well understood. See FIG. 4. BMV has a positive sense, tripartite RNA genome comprising four RNA molecules which are encapsulated in 3, structurally indistinguishable capsids. The length of each sub-genomic cargo is different and so is the sequence, which suggests differences in secondary structure. The capsid can carry genomic cargo of different lengths, and different secondary structures. The lumenal BMV coat protein interface can naturally adapt to reasonably small changes in cargo volume, without a change in the shell structure. The particles have an average diameter of ~28 nm.

Referring to FIG. 4, image "A" shows a structure of BMV coat protein trimer showing the canonical motif encountered in many small icosahedral viruses. Image "B" shows a BMV capsid with the blue and red colors designating positive and negative charge residues, respectively. There are 180 coat proteins in the native BMV shell (triangulation number, T=3), but other magic numbers can be obtained, depending on cargo characteristics (be it RNA or Nano-Particles).

BTV

BTV is an animal virus composed of 10 strands of dsRNA enclosed in two concentric protein shells with icosahedral symmetry forming the virus core. The virus also contains other proteins at the surface. BTV cores consist of 120 molecules of the VP3 subcore protein arranged with pseudo-T=2 icosahedral symmetry, superimposed with 260 trimers of VP7 protein arranged in a T=13 lattice. The particles have an average diameter of ~70 nm and an internal cavity 46 nm in diameter. Its amenability to loading with guest protein and small molecule bioconjugates to surface loops has been demonstrated [24]. Image "C" of FIG. 4 shows a structure of recombinant BTV particle assembled through the deposition of VP7 trimers onto the VP3 subcore.

BTV has twice the BMV diameter, and has two protein shells which can be manipulated independently. BTV further offers the promise of scalability since it can be expressed and assembled in the host plant to final function, without intervention. Furthermore, recombinant expression warrants identity of shell subunits and, thus, a perfectly monodisperse sample. Absence of fluctuations in number and location of chromophores will greatly simplify characterization and analysis.

Generating the Chromophore Array

The present disclosure provides three main modalities of creating a VLP-templated chromophore array: i) chemical modification, by which chromophores are attached covalently to reactive residues of the coat protein, ii) co-assembly, by which chromophores of matching shapes are inserted during assembly in the capsomeric interstices, iii) genetic manipulation, by which the coat protein is genetically engineered with fluorescent proteins expressed on outside loops not participating in assembly interactions. It is within the scope of the present disclosure to generate VLPs utilizing any of the starting viruses as discussed herein according to any of the modalities disclosed herein.

Optical Properties

Applicants have surprisingly discovered that the optical properties of VLP-supported coupled-chromophore arrays are distinct from those of a classical incoherent ensemble of chromophores. For example VLPs of the present disclosure exhibit: directional emission, fast relaxation dynamics, and orders of magnitude increase in brightness, representing particularly appealing characteristics. Added benefits include the possibility of genetic engineering and scalable production. Thus, ultimately, super-radiant VLPs may be entirely produced in plants—an archetypal demonstration of bio-enabled, bottom-up allopoiesis.

The VLPs of the present disclosure emit directional, bright pulses of near-infrared light when illuminated by an ultrafast laser. In certain embodiments the VLP binds specifically to cancerous cells, for example glioblastoma cells. Thus in according with certain embodiments the present disclosure provides a method of treating cancer cells. In one exemplary method the surgeon incubates tissue with a solution of VLPs, washes it, then scans a pulsed laser scalpel with pulse duration shorter than 100 ps over the marked tissue. The light is absorbed by the VLP when the scalpel is above it, then collective fluorescence emission occurs in the form of a burst of light, hundreds of times shorter than the individual chromophore excitation lifetime. This burst of light is read optically and the laser scalpel intensity increased, and if intense enough, is used to destroy the cell to which the VLP is attached.

By using quantum coherent super-radiant VLPs, multivalent binding increases specificity, and super-radiance, i.e. brightness enhancement (by a factor of ~100). This leads to facilitated detection of single cells, and provides a mechanism for removal of marked VLPs by simply scanning a laser scalpel above them. The laser scalpel intensity can be modulated via optical feedback from the VLP for automatic resection, eliminating operator error.

Determining the impact that nearest-neighbor distance, symmetry, total number of chromophores, chromophore orientation, capsid-chromophore interaction, and chromophore-metal nanoparticle interactions may have on the optical properties, specifically on collective relaxation dynamics is highly desirable. To determine these parameters single particle time-resolved spectroscopy and near-field optical microscopy is performed, and virus architecture is manipulated through physical, chemical, and genetic methods.

The following specific Examples are provided to promote a further understanding of certain aspects of the present disclosure. It will be understood that these Examples are illustrative, and not limiting, in character.

EXAMPLE 1

Synthesis of Fluorescent BMV VLPs

Figure 5A:
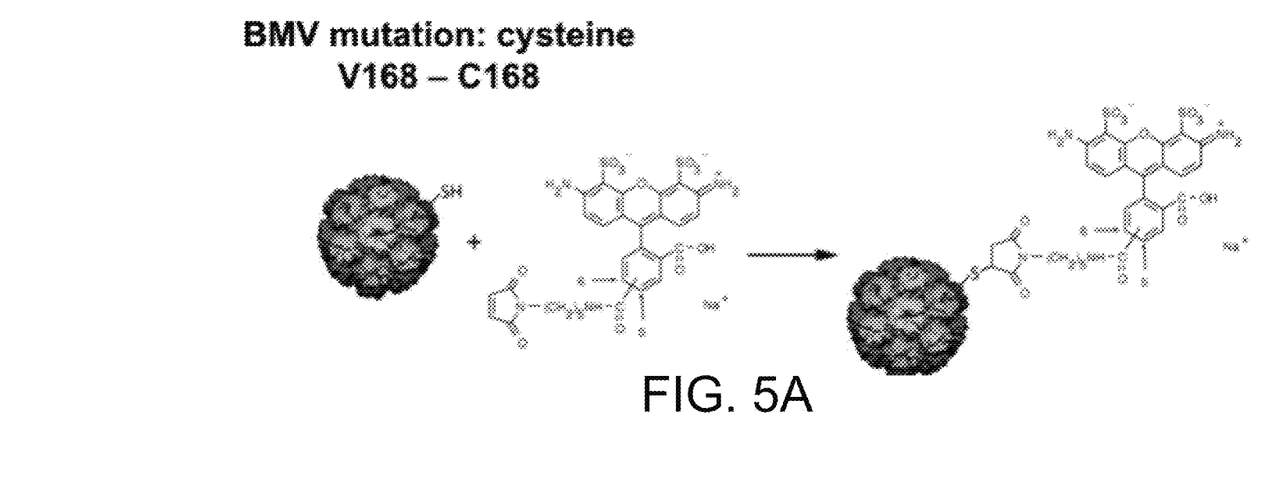
FIGS. 5A-B illustrates various aspects of Fluorescent V168C mutant BMV particles.
Figure 5B:
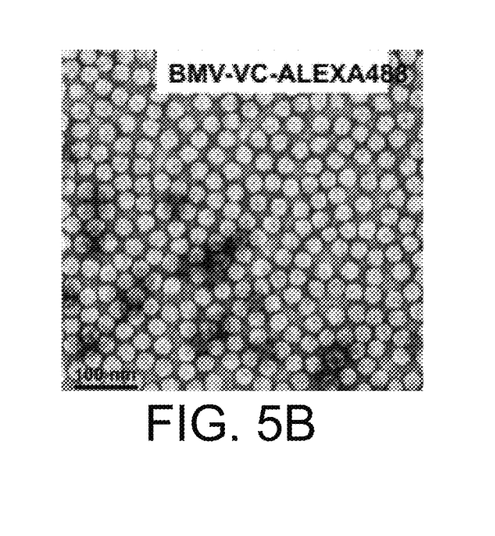

Wild-type BMV (wtBMV) and a BMV mutant (V168C) were obtained. BMV mutant (V168C) displays 180 cysteine residues on the capsid surface that can be bioconjugated with fluorescent dyes and other types of tags through thiol-maleimide chemistry. Alexa Fluor 488 C5 Maleimide was used in experiments with the BMV mutant, see FIG. 5, and yielded the most promising results. The dye-conjugated V168C particles appeared to be more stable to manipulations even than wtBMV, which suggests that the chromophore interacts strongly with the capsid, stabilizing it. Note that wtBMV also has 1440 solvent-exposed lysines, i.e. eight Lys residues per coat protein. Lysines are addressable through reaction with active esters (e.g, succinimidyl, sulfo-succinimidyl, or tetrafluo-rophenyl esters).

Referring to FIG. 5, various aspects of Fluorescent V168C mutant BMV particles are shown. "A" shows the bioconjugation chemistry. Image "B" is a Transmission Electron Microscopy (TEM) image showing efficient assembly in particles similar in size and morphology with wtBMV.

EXAMPLE 2

Fluorescence Lifetime Imaging Micrograph

Figure 5C:
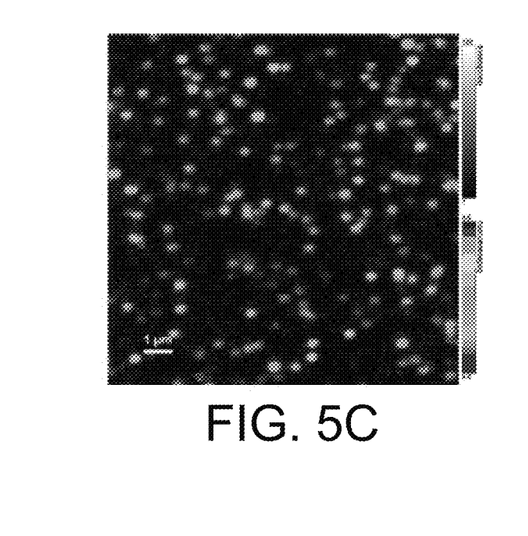
FIG. 5C illustrates Fluorescence lifetime imaging micrograph showing individual fluorescent BMV on glass, in aqueous solution.

FIG. 5 Image "C" shows Fluorescence lifetime imaging micrograph showing individual fluorescent BMV on glass, in aqueous solution. Color map encodes for different lifetimes, which were obtained by single exponential fitting of the fluorescence decay from individual particles.

Fluorescence lifetime imaging microscopy reveals (FIG. 5C) visible variations among individual fluorescent BMV particles. Such heterogeneity is a challenge inherent of the biochemical conjugation method which comes with the possibility of variability in the number of chromophores per particle. However, this also gave an indication that emission lifetime may depend on the number of chromophores. Chromophore titration in the conjugation protocol yielded a progression of <N> values spanning roughly from 15 to 150 (from absorbance and mass spectrometry) which allowed a systematic observation of intensity and lifetime dependence on N by fluorescence life-time imaging microscopy (FLIM). Thus, for most particles having N≤100, behavior consistent with concentration quenching was observed, FIG. 6A-B. However, as N increased above ~100, very bright particles with short lifetimes appeared (blue-purple in color, FIG. 6A), i.e. suppression of concentration induced quenching was observed. To explain the observed change with a concentration quenching model, the data below N≈90 can be fit, but not the data above this value, FIG. 6B. Another interesting aspect of raw data is the existence of "ringing" in the decay at high <N>, FIG. 6C. All these observations led to the hypothesis that relaxation of the fluorescent V168C mutant is at least partly coherent.

Figures 6A, 6B, 6C:
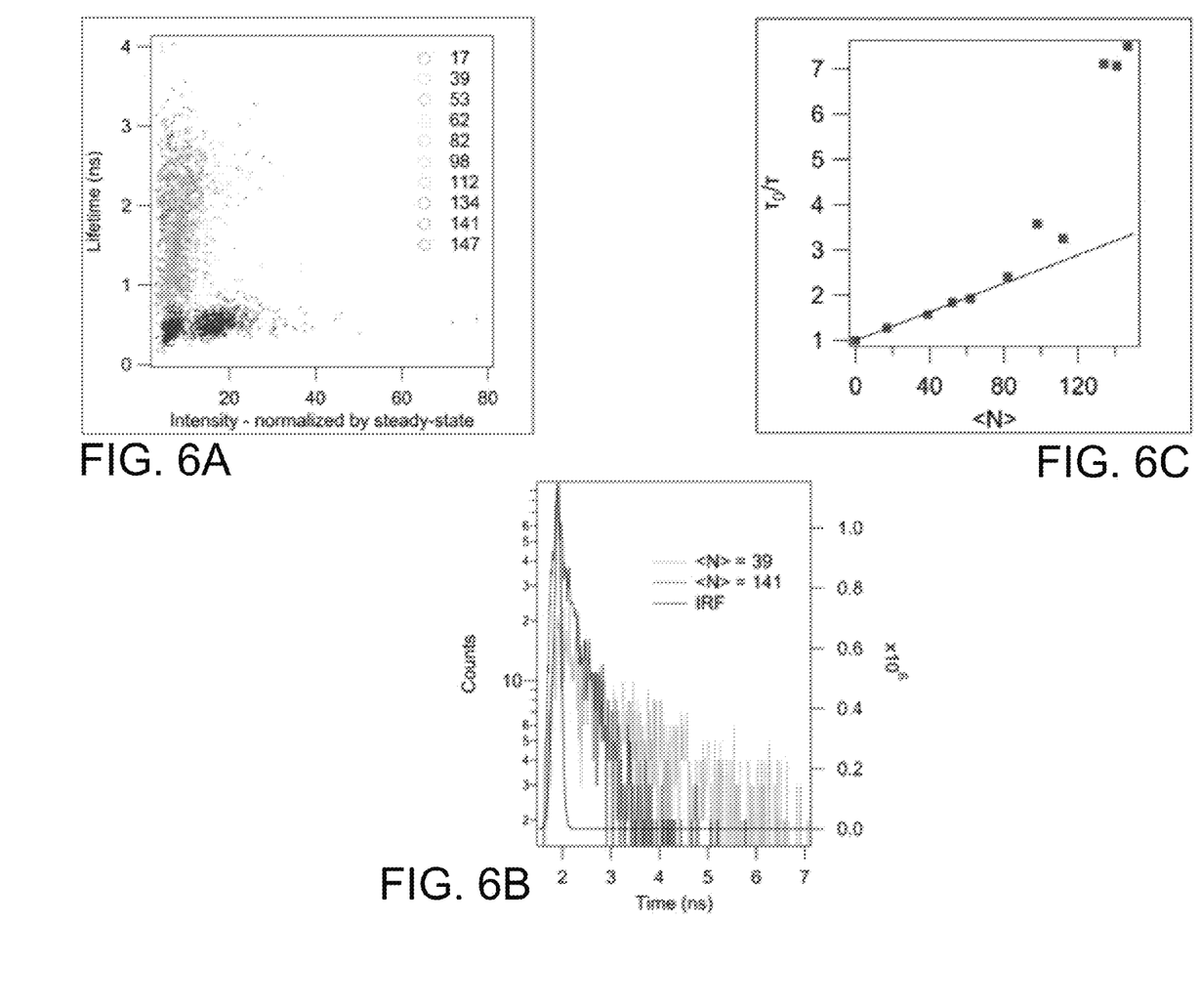
FIGS. 6A-C illustrate fluorescence life-time imaging data.

Referring to FIG. 6, image "A" provides fluorescence life-time imaging data showing the correlation between intensity of light emission and its lifetime. Each data point is from a single particle. Colors encode for <N>. Image "B" illustrates the ratio between the unperturbed, individual chromophore lifetime ($\tau_0$) and the multichromophore particle lifetime ($\tau$) as a function of <N>. The black line: expected $\tau_0/\tau$ on <N> from the concentration quenching model. Image "C" is the raw photon arrival time histograms after a ps laser pulse (instrumental response function, IRF, in black, right axis scale) for <N>=39 (orange) and <N>=141 (blue).

EXAMPLE 3

Spectroscopic Studies of Multi-Chromophore VLPs

Combined Absorption and Time-Resolved Fluorescence

FLIM measurements provide access to excited state decay, which in turn depends on both radiative and non-radiative relaxation rates. To determine the radiative lifetime as a function of N, we have to determine the fluorescence quantum yield, $\Phi_F$, is determined as shown in Equation 5:

$$\Phi_F = \frac{1}{E_{abs}} \int_0^\infty i_F(t)dt = k_r^S \tau_S \qquad (5)$$

where, $k^S_r$ is the rate constant for radiative relaxation, $\tau_s$ is the lifetime of excited state (obtained from FLIM), $E_{abs}$ is the absorbed energy, $i_F(t)$ is the fluorescence intensity as a function of time after ultrafast excitation.

In order to find $k^S_r$, $E_{abs}$ is measured. This is accomplished by photothermal absorption microspectroscopy, a low-background technique, capable of measuring pure absorption cross-sections of single nanoparticles. For this, the current photothermal microscopy setup is modified to allow for simultaneous measurements by FLIM and photothermal absorption spectroscopy. The changes are straightforward, using a photothermal microscopy setup employing a 200 ps supercontinuum laser (76 MHz, λ=450-750 nm) as heating source. Pulse repetition rate is adjusted according to the type of experiment: 3 MHz for absorption and 76 MHz for fluorescence lifetime by time-correlated single photon counting (TCSPC). Photothermal signal detection is done with two Si pin photodiodes, matched for balanced detection of the 800 nm probe beam, and a lock-in amplifier. Gold NPs of known diameter are used for calibration. The fluorescence channel will use a photon counting detector connected to a TCSPC card.

In a zeroth order approximation estimate, the heat released from a collection of 200 chromophores with a quantum yield of ~0.5 is of the same order of magnitude with that of a Au NP of 1.5 nm radius, i.e. in principle detectable.

EXAMPLE 4

Spectroscopic Studies of Multi-Chromophore VLPs

Pump-Probe Transient-Absorption Spectroscopy

Since excited state relaxation dynamics is strongly dependent on intra- and intermolecular fluctuations, which in turn could, in great measure, depend on chromophore-template interactions, transient absorption spectroscopy is used to determine the role of the virus template in the collective relaxation process. Briefly, ultrafast, 150 fs pulses from an optical parametric amplifier pumped by a Ti:sapphire regenerative amplifier at 250 kHz repetition rate is used to pump the $S_1$ state of the system. White-light pulses (450-750 nm) pass through the sample at variable time delays (0-2 ns) provided by a high-resolution, closed-loop translation stage, and are spectrally analyzed by a f/3 Czerny-Turner monochromator. Transient absorption spectra is collected as a function of N, and also, of environmental variables that likely control template fluctuations (pH, temperature, osmotic pressure; see below).

This setup can also take advantage of the photothermal effect, which is present (albeit in ensemble form, not on a single particle basis). Thus, the excited state relaxation rate is determined from the fast initial decay, while the total amount of heat from intramolecular non-radiative relaxation is estimated via data constraint heat flow modeling, at least relatively, from the trailing portion of the transient absorption curve, which is caused by the photothermal lens effect.

EXAMPLE 5

Spectroscopic Studies of Multi-Chromophore VLPs

Mapping the Emission Pattern

Coherent relaxation is directional, along the k→vector of the incident field. Determination of the emission pattern in a quantitative way allows for the clear discrimination between possible relaxation modes, and quantitative knowledge of the three dimensional emission map can guide the design of laser-guided surgery devices. Specifically for laser-guided applications, if a laser scalpel includes a sensing device for SR emission, a feedback loop can fire an ablation shot each time the scalpel scans across a target cell-bound particle.

Optical field mapping is performed in which the tip of a near-field probe is scanned in a vertical plane which contains the emitting VLP. The number of photons is collected by the aperture probe at each point, thus revealing the spatial characteristics of the emission.

Figure 7:
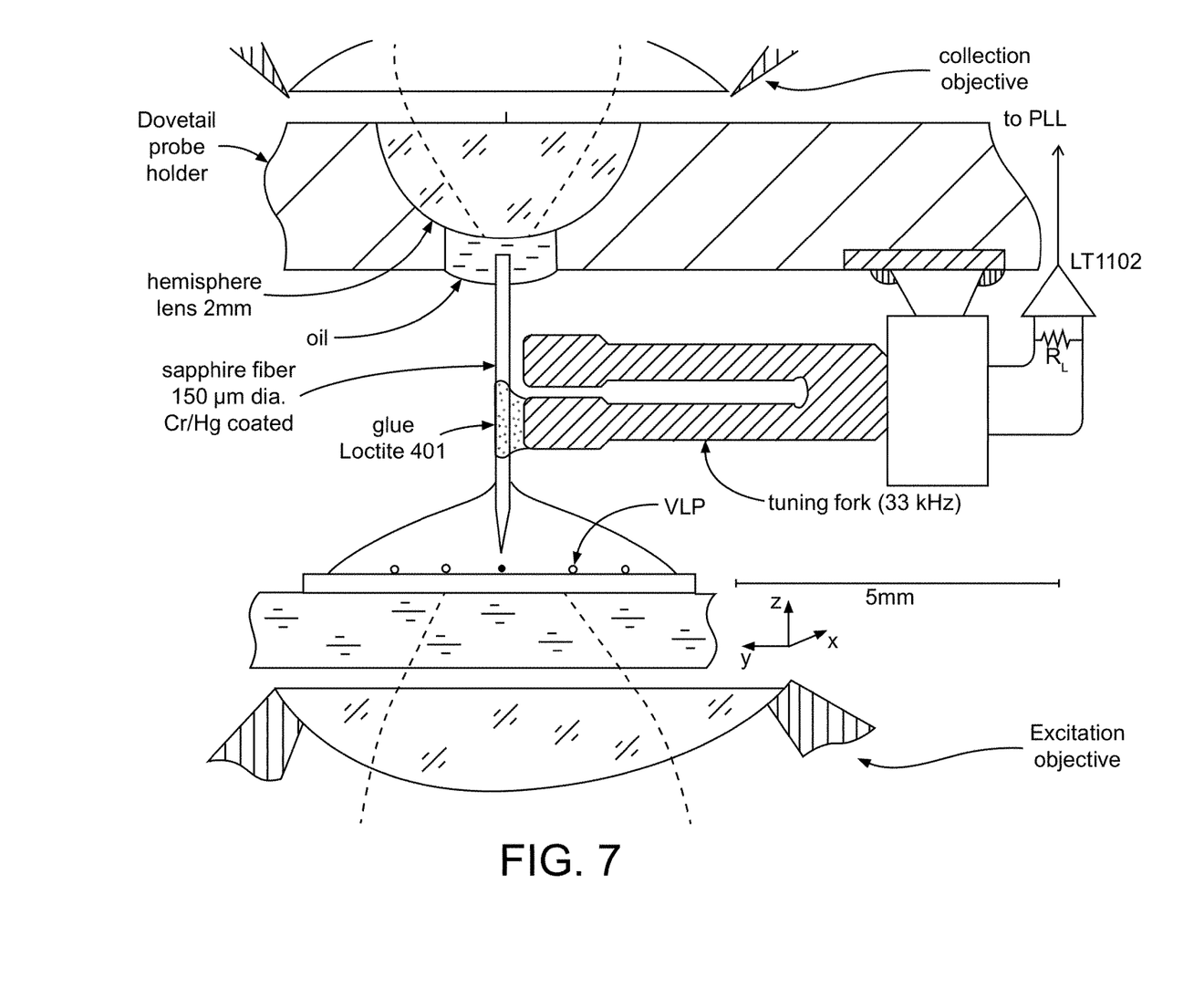
FIG. 7 is a drawing of one embodiment of the head assembly for the near-field scanning optical probing of the emission pattern from single VLPs.

The probe is a short section of sapphire optical fiber, 150 µm diameter, ~4 mm long mounted on one prong of a quartz tuning fork. A drawing of one embodiment of the probe is shown in FIG. 7. The fiber is laterally Al-coated and end-polished using a focused ion beam instrument to obtain a small aperture (~50 nm diameter) for light collection. The output end is immersed in index matching oil. Collected light then goes into a 2 mm diameter hemispheric lens rigidly embedded in the probe holder and is transferred to the emission objective (air, NA=0.75), which optically conjugates the fiber end with a pinhole, for low background. Detection is via a single-photon avalanche photodiode detector (SPAD, 25 cps dark current).

Referring to FIG. 7, there is shown a drawing of the head assembly for the near-field scanning optical probing of the emission pattern from single VLPs. The probe/sample distance is controlled using the tuning fork frequency shift that occurs as the probe explores the vicinity of the substrate surface, in tapping mode. A phase-lock loop approach to frequency-shift measurement ensures high sensitivity to tip-sample forces and ~1-150 nm vertical range.

EXAMPLE 6

Spectroscopic Studies of Multi-Chromophore VLPs

Power-Dependence

The above equation (equation 3) suggests that there is a critical population inversion density beyond which the characteristic coherent relaxation time becomes shorter than the dephasing times. Thus, by progressively increasing the pump power density, one should pass from an incoherent regime to a coherent one. Optical measurements discussed are carried out at different peak pump power densities for 3 pulsewidths: 2 ns, 200 ps, and 150 fs.

EXAMPLE 7

Particle Manipulations

Chromophore Arrangement. Order-Disorder Transitions

Preliminary molecular dynamics simulations suggest that fluorescein tends to nest tightly in the crevices of the virus surface. Conjugated BMV becomes more stable than wtBMV and molecular dynamic (MD) observations support the idea of an intimate interaction between the chromophore and the virus shell.

A straightforward way to add dynamic disorder is to increase the ligand length. This provides more flexibility and presumably pushes the chromophore out in solution. Note that an increase in surface disorder can also be obtained by increasing the temperature to ~75° C., where BMV undergoes an order-disorder transition.

Moreover, it is well known that plant viruses such as BMV undergo a global conformational transition under pH increase (from 5.0 to 7.0) and addition of chelating agents. The high-pH structure is more open, with particle diameter being ~10% larger. The particle is softer, and less thermodynamically stable. Intensity readings are control-corrected for intrinsic pH-dependent fluorescein emission (protonated form has lower fluorescence than de-protonated).

Finally, the addition of an osmolyte (2.5% PEG or dextrane, MW~6000) to a solution of virus particles increases the stiffness of the particles as measured by AFM, by 150%. This presumably occurs by osmotic pressure suppression of shell fluctuations.

EXAMPLE 7

Encapsulation of Metal Nano Particles

The role and efficiency of surface plasmon coupling in Nano Particle-VLPs is determined by the rate of fluorescence emission from Au Nano Particle-VLPs encapsulated in a chromophore-studded virus shell.

Preliminary FLIM data obtained from single VLPs show a sharp peak at very short times, below the resolution limit, which is absent in particles without a metal core (data not shown). Transient absorption spectroscopy provides a lower limit estimate for the actual relaxation time, even if it cannot be accessed it by TCSPC.

Note that besides profoundly affecting relaxation mechanisms, the Nano Particle-templated approach enables a change in the diameter (hence N) and even the symmetry of the shell.

EXAMPLE 8

Stimulated Emission Test

Pump Power Dependence of Emission Spectra

Because of the positive, feedback from the surface plasmon resonance, conditions for stimulated emission are expected to occur at peak power densities similar to those provided by the ultrafast OPA. The following estimate is instructive. The volume of the T=3 virus shell (gain medium) is, Equation 6:

$$V_{shell} = 4\pi a^2 \cdot d_a \approx 10^{-17} \text{ cm}^3 \quad (6)$$

where $a=13.5\times10^{-7}$ cm is the CP shell radius and $d_a=4\times10^{-7}$ cm is the shell thickness. Considering the experimental value of max ~170 dyes per T=3 VLP, the effective density is $\approx 2.0 \approx 10^{19}$ cm$^{-3}$. This effective density is above the threshold density for lasing of $6\times10^{18}$ cm$^{-3}$ reported in ref.

Furthermore, the order of magnitude for the required dye density can be estimated by asking that it be at least twice the population inversion threshold for the laser oscillation to start in a resonant cavity of given quality factor, Equation 7:

$$\Delta N_{th} = \frac{\omega}{Q\sigma(\omega)c} \quad (7)$$

where $Q \approx 8$ is the quality factor for a Au particle and $\sigma(\omega)=10^{-16}$ cm$^2$ is the absorption cross-section of the dye molecule, considered unperturbed by metal. These numbers yield: $\Delta N_{th} \approx 10^{19}$ cm$^{-3}$.

The power density required for population inversion by optical pumping can be estimated from Equation 8:

$$I_p = \frac{h\nu_p}{\sigma_p \tau} \quad (8)$$

where $\tau \approx 2$ ns is the lifetime of the upper level for the lasing transition and $\tau_p \approx 2\times10^{-19}$ cm$^2$ is the absorption cross section. Considering $h\nu_p \approx 2$ eV, we obtain a power density threshold of $I_p \approx 10^6$ W/cm$^2$, which is straightforward to obtain by focusing the 10 mW OPA beam to ~100 μm.

A study of the emission spectrum as a function of the pumping rate and VLP characteristics (spectral overlap, N, diameter) determines conditions for which the spectral narrowing expected for the onset of amplification by stimulated emission would occur. To verify that the observed lasing is indeed originating from individual particles and not from random lasing facilitated by multiple scattering, sample concentration is decreased. Spectral narrowing should not be affected.

At the highest pumping rates, adverse effects may be encountered such as dye bleaching and heat degradation of the protein coat. A capsid protein shell maintains its structural integrity to high steady-state temperatures (~80° C.) and potentially higher to pulsed heating at low repetition rate. However, increasing the density of dyes on the surface is possible by optimizing reaction conditions (e.g. choice of dye, linker, fine tuning the pH, chemically addressing surface-accessible lysines). A distinct possibility in this respect is to employ nanorods (NR) instead of nanospheres. Higher number of dyes per particle, higher quality factors Q and lower losses should be achievable, all at the same time. Preliminary studies showed that stable NR VLPs can be efficiently obtained from BMV capsid protein, FIG. 8. Like in the icosahedral VLPs, chromophores are organized in a layer at ~5 nm distance from the metal surface and regularly distributed in a symmetric pattern.

Figure 8:
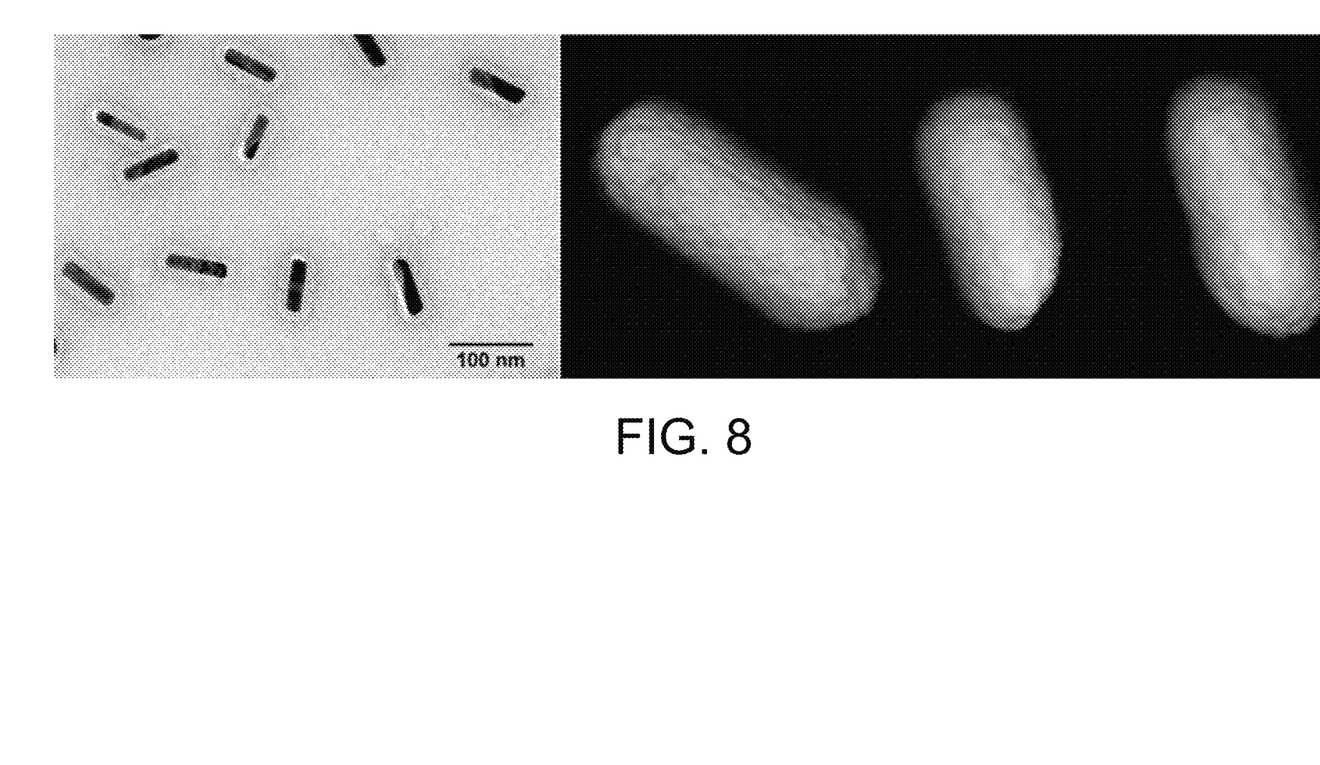
FIG. 8 illustrates exemplary nanorod virus-like particles according to the current disclosure.

Exemplary nanorod VLPs (NR-VLPs) are shown in FIG. 8. On the left is a TEM image showing efficient encapsulation of Au rods of 12 nm diameter. On the right are AFM images showing the regular pattern formed by capsomers in individual NR-VLPs (note chirality).

EXAMPLE 9

BTV-VLPs with Red Fluorescent Proteins

BTV VLPs are expressed and red fluorescent proteins (RFPs) are fused to the VP3 structural protein resulting in 120 RFPs/particle. RFP-BTV is compared to BMV in terms of collective lifetime and fluorescence intensity with BMV, FIG. 6. Coupling and collective response is of RFP-BTV is optimized by exploring different linkers and fusion locations, with guidance from MD simulations. After the optical optimization step, loops on the BTV surface are identified which can be used to fuse CTX, and obtain an RFP-CTX-VLP to be tested against specific cellular binding.

EXAMPLE 10

Detection of VLPs Binding to Glioblastoma Cells

BTV-RFP-CTX particles are generated as described above. Cellular binding and detection of BTV-RFP-CTX particles will be tested using the FLIM instrument. Binding to the CTX target molecules (the matrix metalloproteinase-2 and the chloride channel-3) effects on the collective optical response is tested. Binding should not affect the collective optical response because the RFPs are distributed on the inside interface, while the CTX is on the outside of the shell. However, it is known that, in viruses, binding to membrane receptors can sometimes trigger deep allosteric changes in virus structure.

Human-derived glioblastoma multiforme cell lines are incubated in the presence of targeted (BTV-RFP-CTX) or nontargeted (BTV-RFP) particles at concentrations of 10-100 μM. The samples are then washed and the cellular accumulation of VLPs is determined by confocal fluorescence microscopy. Lifetime measurements from single bound VLPs is performed by FLIM.

What is claimed is:

1. A method of forming a collection of virus-like particles (VLPs), the method comprising:
    obtaining virus capsids having surface-reactive groups; and
    chemically conjugating an array of N chromophores with the surface-reactive groups of each capsid, the N chromophores per capsid being sufficient to achieve collective behavior for the collection of VLPs, resulting in suppression of fluorescence quenching and collective spontaneous emission by the VLPs.

2. The method of claim 1, wherein said chemically conjugating comprises treating the virus capsid with maleimide.

3. The method of claim 1, wherein said array of chromophores is derived from fluorescein.

4. The method of claim 1, wherein the capsid is derived from Brome Mosaic Virus.

5. The method of claim 4, wherein the Brome Mosaic Virus comprises a V168C mutant.

6. The method of claim 4 in which N is greater than 100.

7. The method of claim 1 in which the collective emission, in the absence of a resonator is selected from the group consisting of super-radiance (SR), super-fluorescence (SF) and amplified spontaneous emission (ASE).

8. The method of claim 7 in which the collective spontaneous emission of the collection of VLPs is in the form of super-radiance directly from a coherent stated formed by an incident laser field.

9. The method of claim 7 in which the collective spontaneous emission of the collection of VLPs is in the form of super-fluorescence resulting from rapid intramolecular relaxation at the end of which chromophores are incoherent, followed by formation of a macroscopic dipole through coupling via vacuum fluctuations, followed by collective emission.

10. The method of claim 7 in which the collective spontaneous emission of the collection of VLPs is in the form of amplified spontaneous emission based on dye molecules absorbing light and then decaying by spontaneous emission.

11. The method of claim 1 in which the collective spontaneous emission is in the form of an anisotropic emission comprising a short burst of duration $\tau_p \alpha T_1/N$.

12. The method of claim 1 in which collective spontaneous emission is characterized by directional emission, fast relaxation dynamics, and orders of magnitude increase in brightness.

13. The method of claim 1 in which the VLPs emit directional, bright pulses of near-infrared light when illuminated by an ultrafast laser.

14. The method of claim 1 in which the conjugating is selected from the group consisting of spontaneous organization of protein and cargo, and expression and self-assembly of modified coat protein in plants.

15. The method of claim 14 in which the conjugating is self-assembly.

16. The method of claim 1 in which the conjugating forms VLPs having an average diameter of less than 150 nm.

17. The method of claim 16 in which the conjugating forms VLPs having an average diameter of 20-80 nm.

18. The method of claim 17 in which the conjugating forms VLPs having an average internal cavity diameter of 40-50 nm.

* * * * *